United States Patent [19]

Jefferies

[11] Patent Number: 4,961,706
[45] Date of Patent: Oct. 9, 1990

[54] METHOD FOR OBTAINING A BAND TECHNIQUE DENTAL IMPRESSION

[75] Inventor: Steven R. Jefferies, Milford, Del.

[73] Assignee: Dentsply Research & Development Corp., Milford, Del.

[21] Appl. No.: 216,050

[22] Filed: Jul. 7, 1988

[51] Int. Cl.$^5$ ............................................. A61C 9/00
[52] U.S. Cl. ..................................... 433/214; 433/40; 433/39
[58] Field of Search .................. 433/39, 40, 214, 37, 433/48

[56] References Cited

U.S. PATENT DOCUMENTS

| | | | |
|---|---|---|---|
| 2,758,374 | 8/1956 | Fisher et al. | 433/37 |
| 3,530,585 | 9/1970 | Goldstine | 433/40 |
| 4,468,202 | 8/1984 | Cohen | 433/199 |
| 4,491,453 | 1/1985 | Koblitz et al. | 433/217 |
| 4,500,288 | 2/1985 | von Weissenfluh | 433/40 |
| 4,543,063 | 9/1985 | Cohen | 433/175 |
| 4,553,936 | 11/1985 | Wang | 433/37 |
| 4,704,087 | 11/1987 | Dragan | 433/40 |
| 4,718,849 | 1/1988 | von Weissenfluh | 433/29 |
| 4,761,136 | 8/1988 | Madhavan et al. | 433/214 |
| 4,781,583 | 11/1988 | Lazarus | 433/39 |
| 4,813,875 | 3/1989 | Hare | 433/214 |

OTHER PUBLICATIONS

Theory and Practice of Crown and Bridge Prosthodontics, (30 pages), Stanley et al., 5th Ed., 1965, C. V. Mosby Co., pp. 542-553, 572-587.

*Primary Examiner*—Cary E. Stone
*Attorney, Agent, or Firm*—D. James Picciano; David E. Wheeler; Edward J. Hanson, Jr.

[57] ABSTRACT

The invention relates to a method of preparing a dental impression using an improved band technique. The method comprises placing an actinic light transparent band containing light polymerizable impression material over a tooth or a tooth preparation, and polymerizing the impression material and contacting the band with the polymerized impression material with tray impression material and incorporating the band into the overall impression.

8 Claims, 1 Drawing Sheet

METHOD FOR OBTAINING A BAND TECHNIQUE DENTAL IMPRESSION

The present invention relates to a method for obtaining a dental impression using an improved band technique.

BACKGROUND

In order to obtain a dental impression of a single tooth, particularly for three-quarter and complete crown preparations, it is desirable to retract the gum and expose the gingival margin. One suitable method for obtaining such an impression is known as the Pagenkopf technique, which is described by Tylman et al in "Theory and Practice of Crown and Bridge Prosthodontics," fifth edition, 1965, published by C. V. Mosby Co. In the Pagenkopf technique a copper band, just a little larger than the greater circumference of a tooth is festooned, and the gingival end of the copper band is crimped and pinked with crimping pliers. A washer, stamped out of buckskin, chamois, felt or similar material is saturated with an astringent. First the washer and then the band are placed over a tooth preparation and pressure is applied until the washer is forced beyond the gingival line. The crimped and pinked edged of the band prevents the washer from slipping either inside or outside of the band. The band is filled with impression material and is left in position about ten minutes. An impression is then taken, wherein the festooned copper band is incorporated into the tray impression material.

When using the Pagenkopf technique, there is always some concern by the practitioner whether or not the copper band and washer shift when contacted with the impression material in the tray. It is especially time consuming to wait 10 minutes for a first band impression and an additional 10 minutes for the second tray impression to cure before the final impression is completed. Also it is time consuming to festoon and pink the copper band and to prepare the buckskin washers. It is an object of the present invention to overcome the shortcomings of the prior art technique.

SUMMARY OF THE INVENTION

The present invention provides a method for obtaining a dental impression comprising the steps of filling an actinic light transparent band of material with a light polymerizable impression material placing said filled band around a prepared tooth, (such as a tooth that has been prepared for a crown), and applying actinic light to the impression material thereby polymerizing the impression material. Light curing offers shortened times to cure, typically 1 minute or less, preferably 20 seconds or less. After cure of the impression material within the band on the tooth, additional impression material can be applied to the band and its surrounding structures, and an impression tray containing additional impression material may be brought into contact therewith, and cured by means well known in the art.

DETAILED DESCRIPTION OF THE ILLUSTRATED EMBODIMENT

Figure 1:
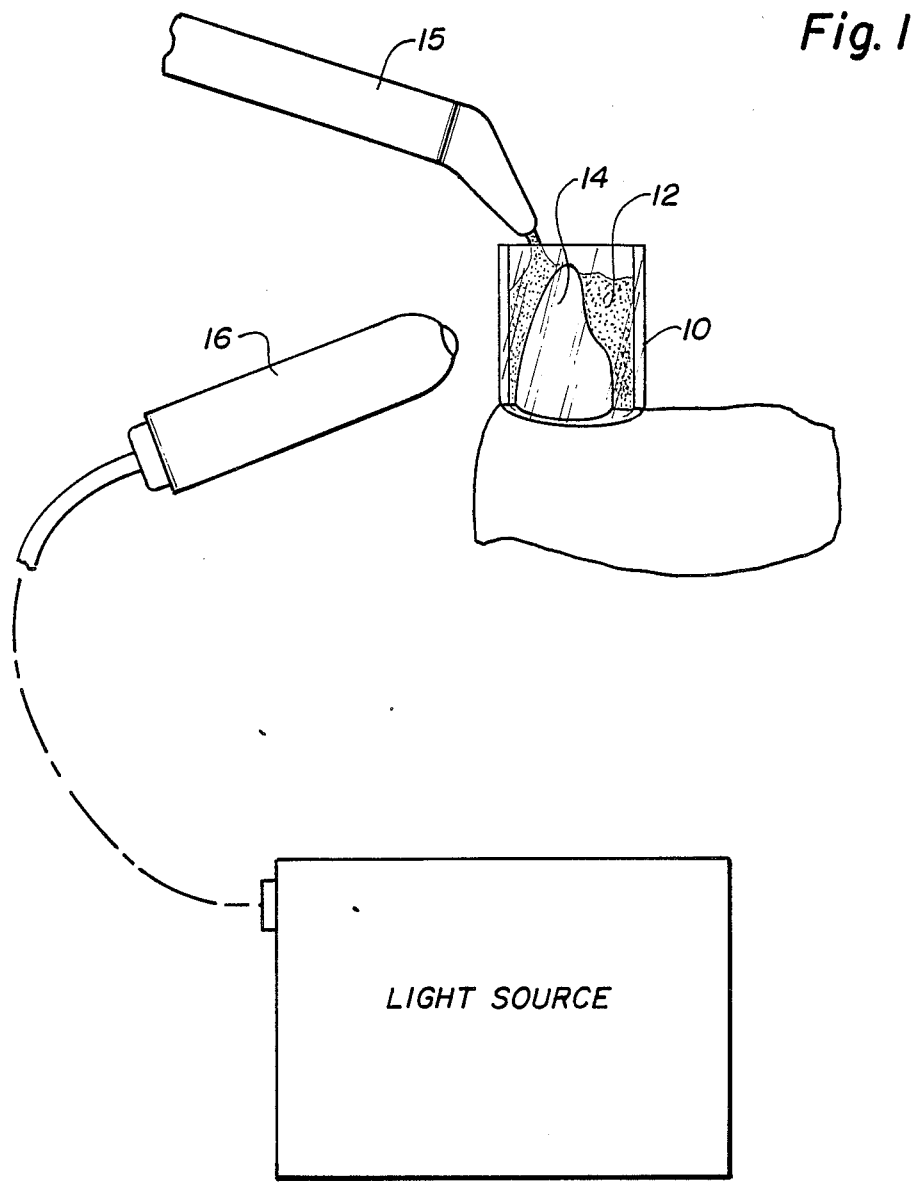
FIG. 1 illustrates a prepared tooth having a band and impression material proximal thereto.

Referring now to FIG. 1, in the method of the invention, an actinic light transparent band 10 filled with light polymerizable impression material 12 is first placed around the tooth or other prepared dental structure 14. The band used may be a plastic dental matrix which is used to prepare restoratives (described in U.S. Pat. No. 4,523,909 to Lazarus, the disclosure of which is incorporated herein by reference) a modified version thereof, a clear continuous sleeve formed of mylar or cellulose acetate or the like or other similar band. The band 10 is placed in a manner that tends to displace the gingival margin around the tooth. The band may be made of a relatively soft and/or flexible plastic, obviating the need for a washer which is suggested for use in prior art methods.

The impression material used to fill the band is preferably a syringable impression material (light body) such as disclosed in copending application U.S. Ser. No. 120,269, filed Nov. 13, 1987, said application being incorporated herein by reference. Those skilled in the art will recognize that using the present method more viscous impression materials, even heavy body impression materials (as disclosed in SN 120,269) may be used to fill the band in the initial step of the method.

The impression material is then polymerized by applying actinic light having a wavelength of between about 360–600 nm for a time sufficient to affect said polymerization using a light 16 designed for that purpose such as a PRISMETICS ® light, a product of The L. D. Caulk Company, a Division of Dentsply International Inc. After curing, the band and impression material are very stable on the tooth.

It has been found that using the method of the invention, the practitioner has the ability to interrupt the method and remove the band, after the impression material has been cured, to examine the internal detail of the first impression. In replacing the band, the practitioner is able to see the precise reseating of the impression material on the tooth preparation. Such a reseating is not feasible with a copper band and a self-cured impression material. An examination step and reseating are made possible because of the transparent band and because of the translucent properties of the cured impression material.

Optionally, the practitioner may add additional syringable material to the impression, replace the band on the preparation, and cure the added impression material with actinic light in the same manner as before.

When the impression has been reseated, additional syringable two-component self-cured or light cured impression material optionally may then be added to the area to be further impressed using syringe 15. An impression tray, containing a more viscous impression (heavy body) material, is then brought into contact with the site. An impression of the area is then completed in a manner known to those skilled in the art using self-cured or light activated tray impression material in a manner described in copending Ser. No. 120,269.

In a preferred embodiment the band may be coated with a biocompatible adhesive to assure its retention to the tray impression material. In a preferred embodiment, such an adhesive may be formulated to cross link either to a light polymerized or a self-cured impression material.

Alternatively, the band may have perforations that permit the extrusion of impression material through the band and contact and cross-linking of the band impression material with tray impression material, or the band may be fitted with mechanical extensions to interlock the band within the final impression.

The method of the present invention permits an immediate cure on command of the impression material in the band. That is, the practitioner does not have to wait for the impression material to self-cure as is the case in the Pagenkopf technique. Also, using the light curable impression material of the copending application, the practitioner can be assured that the cure will be complete to the degree necessary to stabilize the band so that it does not shift while the tray impression material is applied.

While present embodiments of the invention and methods of practicing the same have been illustrated and described, it will be recognized by those skilled in the art that this invention may be otherwise variously embodied and practiced within the scope of the following claims.

What is claimed is:

1. A method for obtaining a dental impression comprising the steps of
   (a) filling an actinic light transparent, substantially continuous preformed band with visible light polymerizable impression material,
   (b) placing said transparent, substantially continuous preformed band to loosely surround preparations of one or more teeth,
   (c) applying actinic light to said impression material through said transparent band and polymerizing said impression material to form an impression, and
   (d) contacting said band and polymerized impression material with additional impression material covering the band and surrounding structures.

2. The method of claim 1 which comprises applying actinic light having a wavelength of between about 360–600 nm.

3. The method of claim 1 which comprises filling said band with an impression material comprising polyurethane resin.

4. The method of claim 1 comprising the further steps of
   (a) contacting said band and said polymerized impression material with a heavy body impression material, incorporating said band and said polymerized impression material in said heavy body material, and
   (b) curing said heavy body material.

5. The method of claim 1 further comprising the steps of
   (a) contacting said band and polymerized impression material with additional impression material covering the band and surrounding structures.

6. The method of claim 5 which comprises the further step of painting said band with adhesive prior to contacting said band with tray contained impression material.

7. The method of claim 4 which comprises using a band having perforations and permitting the extrusion of impression material through said perforations to permit contact between impression material inside and outside the band.

8. The method of claim 1 further comprising the steps of
   (a) placing an impression material that is substantially transparent when cured in the band around preparations of one or more teeth
   (b) removing the band and impression material from said preparation for examination after at least partial curing by the application of actinic light
   (c) examining the impression and adding additional impression material to the band as needed
   (d) replacing the band on the preparation whereby the transparency of the band and substantial transparency of the impression material allows the practitioner to observe the correct repositioning of the band on the preparation.

* * * * *